(12) United States Patent
Okunuki et al.

(10) Patent No.: US 7,991,114 B2
(45) Date of Patent: Aug. 2, 2011

(54) MULTI X-RAY IMAGING APPARATUS AND CONTROL METHOD THEREFOR

(75) Inventors: Masahiko Okunuki, Akiruno (JP); Makoto Sato, Tokyo (JP); Osamu Tsujii, Kawasaki (JP); Takashi Ogura, Tokyo (JP); Hisashi Namba, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/763,486

(22) Filed: Apr. 20, 2010

(65) Prior Publication Data

US 2010/0266097 A1 Oct. 21, 2010

Related U.S. Application Data

(63) Continuation of application No. PCT/JP2009/003679, filed on Aug. 3, 2009.

(30) Foreign Application Priority Data

Sep. 18, 2008 (JP) .................................. 2008-239754

(51) Int. Cl.
*G01N 23/083* (2006.01)
*H05G 1/60* (2006.01)
*H01J 35/06* (2006.01)
*H01J 35/08* (2006.01)

(52) U.S. Cl. ................. 378/62; 378/9; 378/11; 378/122; 378/124; 378/134; 378/196; 378/197

(58) Field of Classification Search ................. 378/9, 11, 378/12, 22, 25, 26, 62, 122, 124, 125, 134, 378/146, 196, 197
See application file for complete search history.

(56) References Cited

U.S. PATENT DOCUMENTS

| | | | | |
|---|---|---|---|---|
| 6,125,167 | A * | 9/2000 | Morgan | 378/124 |
| 6,229,870 | B1 * | 5/2001 | Morgan | 378/9 |
| 6,333,968 | B1 * | 12/2001 | Whitlock et al. | 378/122 |
| 6,553,096 | B1 * | 4/2003 | Zhou et al. | 378/122 |

(Continued)

FOREIGN PATENT DOCUMENTS

| | | |
|---|---|---|
| JP | 2005-261838 A | 9/2005 |
| JP | 2006-057846 A | 3/2006 |
| JP | 2006-061692 A | 3/2006 |
| JP | 2006-524548 A | 11/2006 |
| JP | 2007-263961 A | 10/2007 |
| JP | 2007-265981 A | 10/2007 |

*Primary Examiner* — Allen C. Ho
(74) *Attorney, Agent, or Firm* — Canon U.S.A., Inc. I.P. Division

(57) ABSTRACT

An X-ray imaging apparatus includes a multi X-ray source which includes a plurality of X-ray focuses to generate X-rays by irradiating X-ray targets with electron beams, a detector which detects X-rays which have been emitted from the multi X-ray source and have reached a detection surface, and a moving mechanism for moving the multi X-ray source within a plane facing the detection surface. The X-ray imaging apparatus acquires a plurality of X-ray detection signals from the detector by causing the multi X-ray source to perform X-ray irradiation while shifting the positions of a plurality of X-ray focuses which the detector has relative to the detection surface by moving the multi X-ray source using the moving mechanism. The apparatus then generates an X-ray projection image based on the plurality of X-ray detection signals acquired by the detector.

20 Claims, 9 Drawing Sheets

U.S. PATENT DOCUMENTS

| | | | |
|---|---|---|---|
| 6,674,837 B1 * | 1/2004 | Taskar et al. | 378/122 |
| 6,947,522 B2 * | 9/2005 | Wilson et al. | 378/125 |
| 6,970,531 B2 * | 11/2005 | Eberhard et al. | 378/26 |
| 6,990,169 B2 * | 1/2006 | Claus et al. | 378/4 |
| 7,082,182 B2 * | 7/2006 | Zhou et al. | 378/10 |
| 7,103,138 B2 * | 9/2006 | Pelc et al. | 378/9 |
| 7,192,031 B2 * | 3/2007 | Dunham et al. | 378/122 |
| 7,567,647 B1 * | 7/2009 | Maltz | 378/21 |
| 7,639,774 B2 * | 12/2009 | De Man et al. | 378/9 |
| 7,809,114 B2 * | 10/2010 | Zou et al. | 378/134 |

* cited by examiner

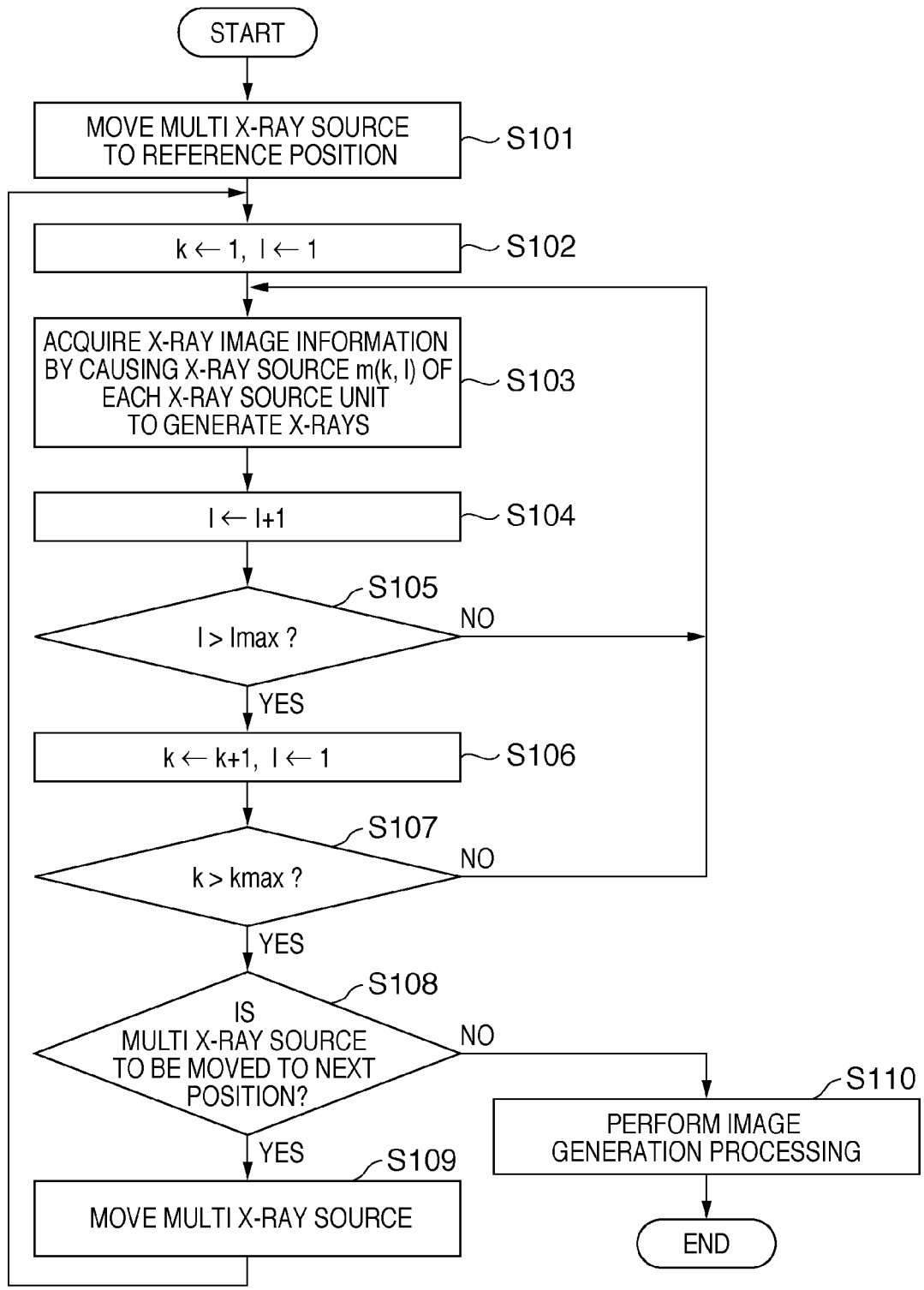

MULTI X-RAY IMAGING APPARATUS AND CONTROL METHOD THEREFOR

CROSS REFERENCE TO RELATED APPLICATIONS

This application is a CONTINUATION of PCT application No. PCT/JP2009/003679 filed on Aug. 3, 2009 which claims priority from the benefit of Japanese Patent Application No. 2008-239754 filed on Sep. 18, 2008, the disclosures of which are hereby incorporated by reference herein in their entirety.

TECHNICAL FIELD

The present invention relates to a multi X-ray imaging apparatus used for nondestructive X-ray imaging, diagnosis, and the like in the fields of medical equipment and industrial equipment using X-ray sources, and a control method for the apparatus.

BACKGROUND ART

A general X-ray tube uses a thermal electron source as an electron source. An X-ray tube of this type generates X-rays on the electron beam incident side by irradiating an X-ray target made of a bulk metal with thermal electrons which are emitted from a filament heated to a high temperature and spread widely. The generated X-rays are then used. A point source type X-ray tube therefore forms a pseudo point X-ray light source by obliquely extracting an elongated X-ray focus. The uniformity of an X-ray intensity distribution has been improved by spacing an X-ray light source apart from the position of an object.

Recently, a cold cathode multi electron source has been proposed as an electron source replacing this thermal electron source. In addition, as an application of this technique, a flat type multi X-ray generating apparatus with a devised method of extracting multi X-ray beams has been proposed (patent reference 1).

Furthermore, it has been proposed to use a multi X-ray source in the field of X-ray CT in which conventional point light source type X-ray tubes have been used. For example, there has been proposed a method of forming a three-dimensional CT image by measuring X-ray transmission data while rotating a combination of a multi X-ray source and a flat type two-dimensional sensor about the axis of an object and moving them along the axis (patent reference 2).

PRIOR ART REFERENCE

Patent References

Patent reference 1: Japanese Patent Application No. 2006-057846
Patent reference 2: Japanese Patent Laid-Open No. 2006-61692

When, however, an X-ray projection image is to be formed by using a multi X-ray source having a plurality of focuses, since the interval between the focuses of the multi X-ray source is about several mm, X-ray transmission data about an object becomes discrete. This makes it difficult to obtain a high-resolution two-dimensional transmission X-ray image.

The present invention has been made in consideration of the above problem, and has as its object to acquire a high-resolution transmission X-ray image by using a multi X-ray source.

SUMMARY OF THE INVENTION

In order to achieve the above object, an X-ray imaging apparatus according to an aspect of the present invention has the following arrangement. That is, the apparatus comprises:
a multi X-ray source which includes a plurality of X-ray focuses to generate X-rays by irradiating X-ray targets with electron beams;
a detector which detects X-rays which have been emitted from the multi X-ray source and have reached a detection surface;
moving means for moving the multi X-ray source within a plane facing the detection surface;
acquisition means for acquiring an X-ray detection signal from the detector for each irradiation by performing X-ray irradiation a plurality of number of times using the multi X-ray source while shifting the multi X-ray source relative to the detection surface by using the moving means; and
generating means for generating an X-ray projection image based on a plurality of X-ray detection signals acquired by the acquisition means.

In addition, in order to achieve the above object, a control method for an X-ray imaging apparatus according to an aspect of the present invention is a control method for an X-ray imaging apparatus including:
a multi X-ray source which includes a plurality of X-ray focuses to generate X-rays by irradiating X-ray targets with electron beams;
a detector which detects X-rays which have been emitted from the multi X-ray source and have reached a detection surface; and
moving means for moving the multi X-ray source within a plane facing the detection surface,
the control method comprising:
an acquisition step of acquiring X-ray detection signals from the detector for each irradiation by causing the multi X-ray source to perform X-ray irradiation a plurality of number of times while shifting the multi X-ray source relative to the detection surface by using the moving means; and
a generating step of generating an X-ray projection image based on a plurality of X-ray detection signals acquired in the acquisition step.

According to the present invention, it is possible to acquire a high-resolution transmission X-ray image by using a multi X-ray source.

Other features and advantages of the present invention will be apparent from the following description taken in conjunction with the accompanying drawings, in which like reference numerals designate the same or similar parts throughout the figures thereof.

BRIEF DESCRIPTION OF DRAWINGS

The accompanying drawings, which are incorporated in and constitute a part of the specification, illustrate embodiments of the invention and, together with the description, serve to explain the principles of the invention.

FIG. 12 is a flowchart for explaining the operation of an X-ray imaging apparatus according to the first embodiment.

DETAILED DESCRIPTION OF THE EMBODIMENTS

The preferred embodiments of the present invention will be described below with reference to the accompanying drawings.

First Embodiment

Figure 1:
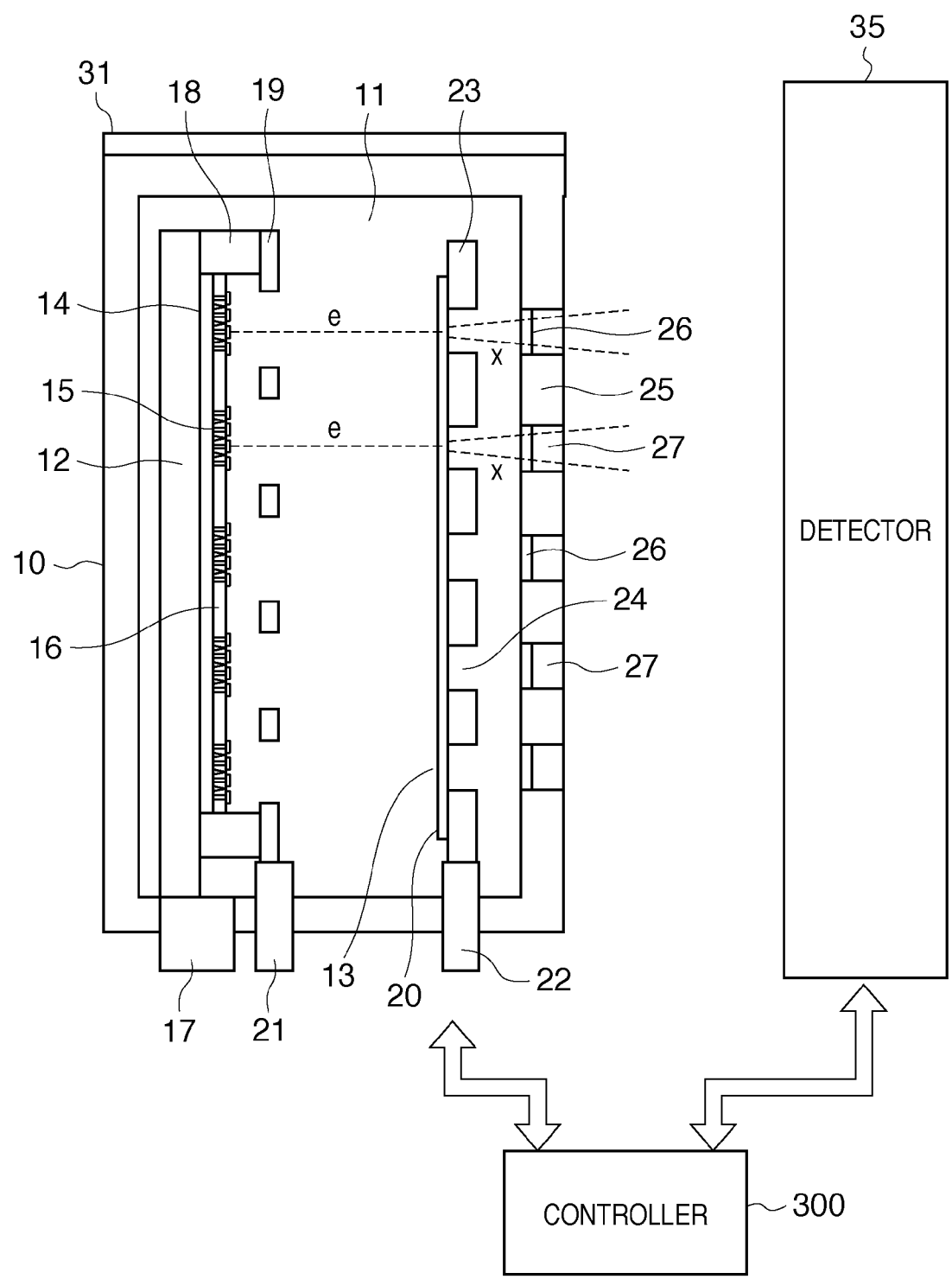
FIG. 1 is a view showing an example of the arrangement of a multi X-ray source body according to the first embodiment.

FIG. 1 is a view showing the arrangement of a multi X-ray source body 10 which has a plurality of X-ray focuses to generate X-rays by irradiating X-ray targets with electron beams. A multi electron beam generating unit 12 and transmissive targets 13 as X-ray targets are arranged in a vacuum chamber 11 of the multi X-ray source body 10. The multi electron beam generating unit 12 includes an element substrate 14 and an element array 16 having a plurality of electron emitting elements 15 arrayed on the element substrate 14. A driving signal unit 17 controls the driving of the electron emitting elements 15. A lens electrode 19 and an anode electrode 20 are provided to control multi electron beams e generated from the electron emitting elements 15. High voltages are applied to the electrodes 19 and 20 via high voltage introduction portions 21 and 22. The lens electrode 19 is fixed to the element substrate 14 through an insulator 18.

The transmissive targets 13 upon which electron beams e emitted from the electron emitting elements 15 impinge are discretely placed in correspondence with the plurality of electron emitting elements 15 to form X-ray focuses, respectively. In addition, the targets 13 are provided with vacuum chamber X-ray shield plates 23 made of a heavy metal. The vacuum chamber X-ray shield plates 23 are provided with X-ray extraction portions 24. Wall portions 25 of the vacuum chamber 11 located in front of the X-ray extraction portions 24 are provided with X-ray extraction windows 27 including X-ray transmission films 26.

The electron beams e emitted from the electron emitting elements 15 receive the lens effect of the lens electrode 19, and are accelerated to the final potential level by portions of the transmissive targets 13 of the anode electrode 20. X-ray beams x generated by the targets 13 pass through the X-ray extraction portions 24 and are extracted to the atmosphere through the X-ray extraction windows 27. The multi X-ray source body 10 is provided with a scanning mechanism 34 for two-dimensionally scanning the multi X-ray source within a plane facing the detection surface of a detector 35. The scanning mechanism 34 moves the position of the multi X-ray source in synchronism with the generation of X-rays from the multi X-ray source.

The detector 35 detects the X-rays which have been emitted from the multi X-ray source and have reached the detection surface. A controller 300 includes a CPU and ROM (not shown) and controls the overall X-ray imaging apparatus according to this embodiment, which includes the multi X-ray source body 10 and the detector 35. That is, the controller 300 performs X-ray irradiation while shifting the multi X-ray source relative to the detection surface by causing the scanning mechanism 34 to move the multi X-ray source. In this manner, the controller 300 acquires a plurality of detection signals by acquiring X-ray detection signals from the detector 35 at the respective positions to which the multi X-ray source has been shifted. The controller 300 then generates an X-ray projection image based on these detection signals (X-ray transmission intensity data) and the positions of the multi X-ray source at the times when the detection signals have been acquired. The X-ray imaging operation of this embodiment will be described in detail below.

Figure 2:
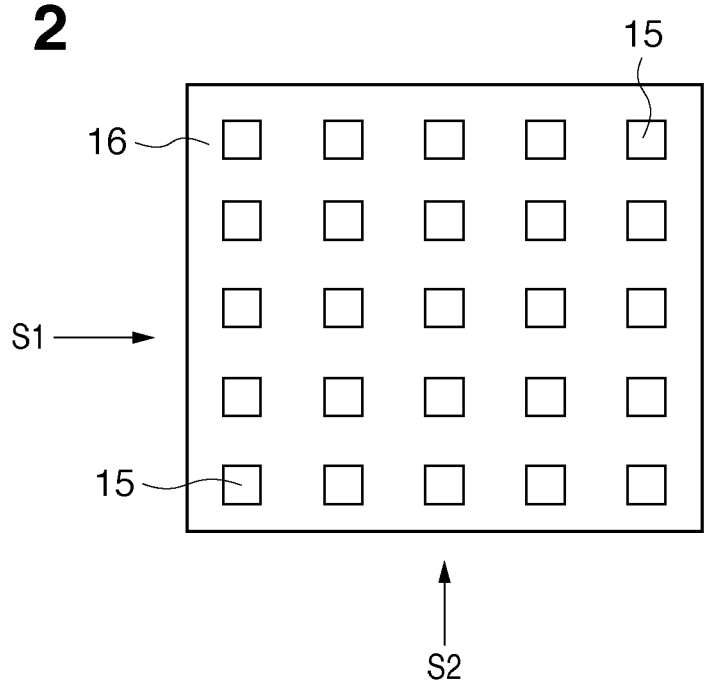
FIG. 2 is a plan view of an element substrate according to the first embodiment.

The electron emitting elements 15 are two-dimensionally arrayed on the element array 16, as shown in FIG. 2. With recent advances in nanotechnology, it is possible to form a fine structure with nm (nanometer) size at a predetermined position by a device process. The electron emitting elements 15 are manufactured by this nanotechnology. The electron emission amounts of the electron emitting elements 15 are individually controlled by driving signals S1 and S2 (to be described later) via the driving signal unit 17. That is, individually controlling the electron emission amounts of the element array 16 by using the driving signals S1 and S2 as matrix signals makes it possible to individually ON/OFF-control X-ray beams constituting a multi X-ray beam.

A cold cathode type electron emitting element can emit electrons by only applying a voltage of several 10 V to several kV to the electron emitting element. An X-ray generating apparatus using this electron emitting element as an electron source therefore need not heat the cathode and requires no wait time for the generation of X-rays. In addition, since no power is required for heating the cathode, a low-power-consumption X-ray source can be obtained even by using a multi X-ray source. Since currents for these electron emitting elements can be ON/OFF-controlled by high-speed driving operation using driving voltages, a multiarray type X-ray source can be manufactured, which selects an electron emitting element to be driven and performs high-speed response operation.

When multi X-ray beams are actually formed, members serving as shield slits for limiting the radiation angles of X-rays generated at the respective X-ray focuses are required near the positions of the X-ray focuses. Therefore, an interval of several mm or more is required in the multi X-ray source.

Figure 3:
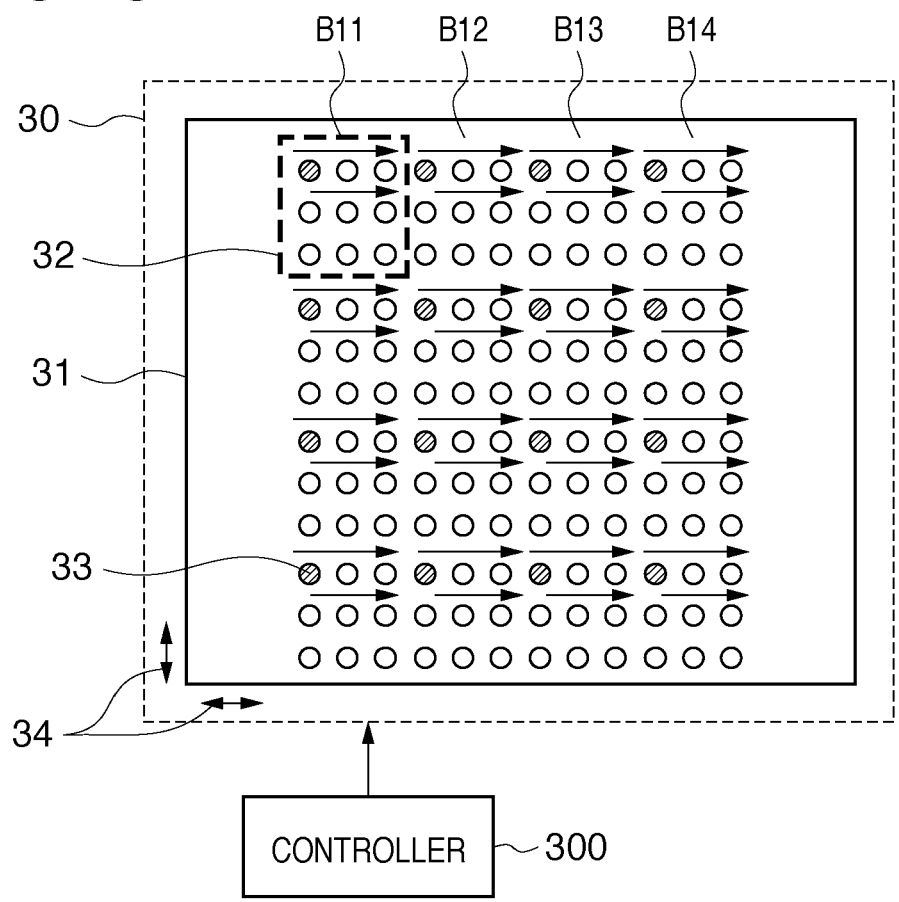
FIG. 3 is a view showing a scanning type multi X-ray source according to the first embodiment.

FIG. 3 is a view schematically showing an example of a scanning type multi X-ray source 30 according to this embodiment, which includes a multi X-ray source 31 having 12×12 X-ray focuses (to be also referred to as X-ray sources hereinafter) arrayed at 20-mm intervals. The multi X-ray source 31 includes multi X-ray units Bij each having an array of 3×3 X-ray sources 33. These multi X-ray units are arrayed in a 4×4 matrix. As shown in FIGS. 1 and 2, each X-ray source 33 includes the electron emitting element 15 and the target 13. Note that the multi X-ray source 31 is controlled such that one X-ray source of each multi X-ray unit 32 generates X-rays in one X-ray irradiation. In each multi X-ray unit 32, the X-ray focuses of the radiation source array are sequentially scanned. The scanning mechanism 34 is provided to move the overall multi X-ray source 31. The scanning mechanism 34 can move the overall multi X-ray source 31 throughout at least the distance between the focuses of the multi X-ray source, that is, throughout the distance between adjacent X-ray focuses. Moving the multi X-ray source 31 using the scanning mechanism 34 is equivalent to moving the multi X-ray source body 10 in this embodiment.

Note that the controller 300 includes a CPU and ROM (not shown) and controls the overall scanning type multi X-ray source 30, as described above. The controller 300 controls the multi X-ray source 31, the scanning mechanism 34, and the detector 35 by executing predetermined control programs, as will be described below, thereby executing X-ray imaging.

Figure 4:
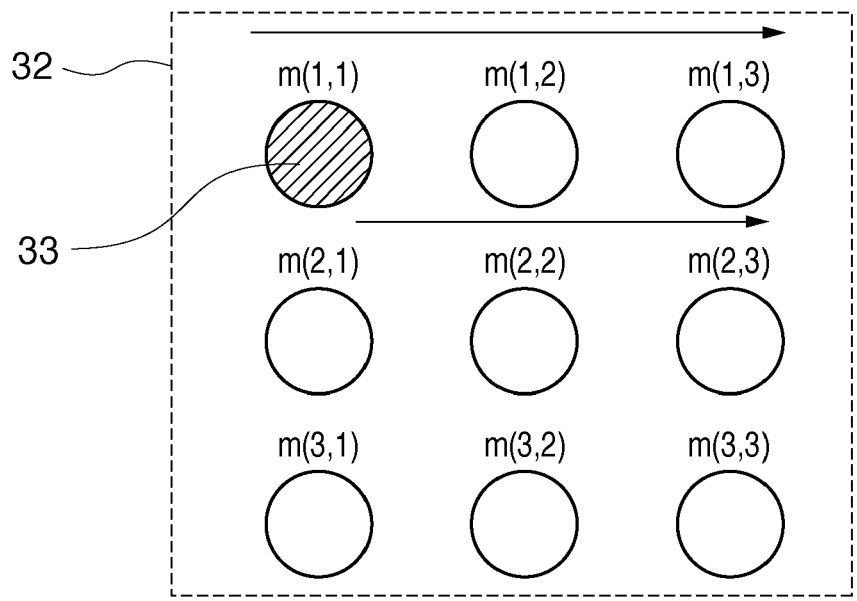
FIG. 4 is a view for explaining the arrangement and scanning of X-ray sources in a multi X-ray unit according to the first embodiment.
Figure 5:
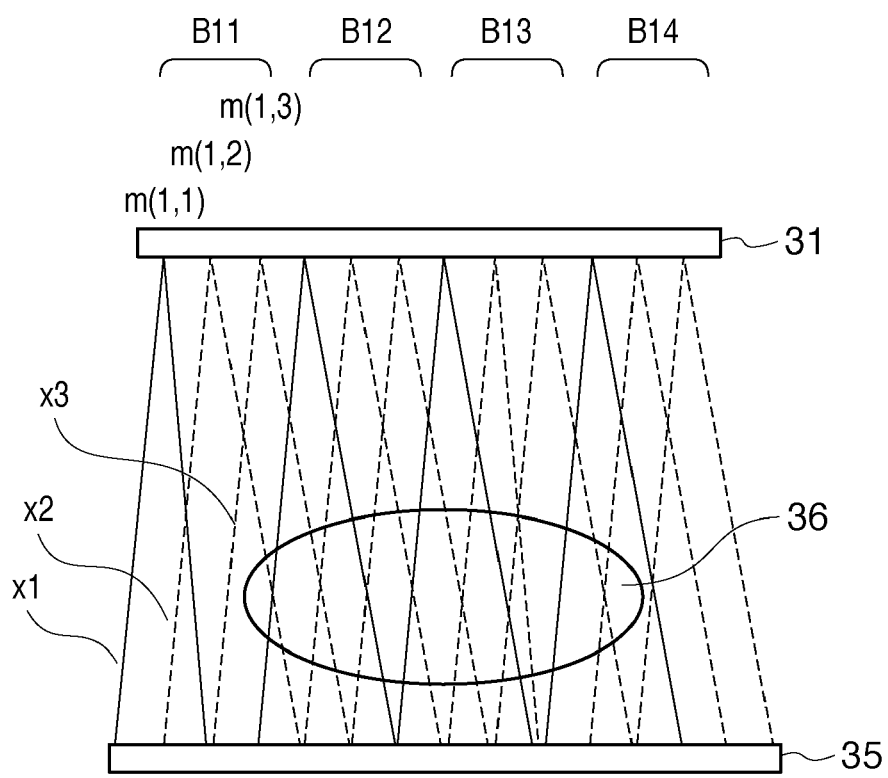
FIG. 5 is a view showing how each X-ray source emits an X-ray beam.

FIG. 4 is an enlarged view of the positions of the X-ray focuses of the multi X-ray unit Bij described above, more specifically, a case in which the position of a generated X-ray source sequentially moves in the order of m(1, 1), m(1, 2), m(1, 3), m(2, 1), . . . . FIG. 5 shows how the X-ray beams generated by X-ray sources of a multi X-ray unit spread. FIG. 5 is a view showing how the multi X-ray source 31 generates X-rays, when viewed from the side, and an array of multi X-ray units B11 to B14 is indicated. In each multi X-ray unit, X-ray sources m(1, 1), m(1, 2), and m(1, 3), which are the X-ray sources in the unit, are arrayed. In this case, reference symbols x1, x2, and x3 denote X-ray beams emitted from the respective X-ray sources.

When the X-ray sources m(1, 1) are to generate X-rays, the X-ray sources m(1, 1) at the positions of the respective multi X-ray units are ready for the generation of X-rays. The divergence angles of the X-ray beams generated from the X-ray sources m(1, 1) of all the multi X-ray units are controlled to prevent interference with each other on the detector 35. This applies to the remaining X-ray sources of the respective multi X-ray units. That is, in this embodiment, all the multi X-ray units simultaneously drive X-ray sources in the order of X-ray sources m(1, 1)→X-ray sources m(1, 3), X-ray sources m(2, 1)→X-ray sources m(2, 3), X-ray sources m(3, 1)→X-ray sources m(3, 3). In other words, the plurality of X-ray sources 33 of the multi X-ray source 31 are divided into groups so as to form groups according to the X-ray focuses of X-rays which do not interfere with each other on the detection surface of the detector 35 even if the X-ray sources are made to simultaneously generate X-rays. That is, in this embodiment, the X-ray sources are grouped such that the X-ray sources m(1, 1) of the respective units belong to the first group, and the X-ray sources m(1, 2) of the respective units belong to the second group. The plurality of X-ray sources 33 are then driven for each group to generate X-rays.

When X-ray irradiation from the X-ray source m(1, 1) is complete and X-ray irradiation from the next X-ray source starts, an X-ray detection signal obtained by this X-ray beam is stored as image data in the memory (not shown) of the controller. In addition, the position of the multi X-ray source 31 at this time is held in the memory for the generation of a projection image. Thereafter, the next X-ray source m(1, 2) is driven to perform X-ray irradiation. While the X-ray sources 33 are sequentially turned on in each multi X-ray unit 32, the X-ray transmission image data of an object 36 is acquired via the detector 35.

The X-ray transmission image data obtained in the above manner is an X-ray image from positions spaced apart from each other by the interval between the X-ray sources (20 mm in this case). For this reason, when a transmission X-ray image is reproduced from these image data, X-rays obliquely and discretely strike the object 36. When, therefore, these data are converted into a projection image, a high-quality projection image cannot be expected because the image data have defects.

In this embodiment, therefore, in order to implement proximity projection imaging with high image quality by eliminating such data defects between X-ray sources, X-ray projection data are acquired by performing X-ray irradiation a plurality of number of times while finely moving the position of the multi X-ray source 31 in FIG. 3 using the scanning mechanism 34. Using the scanning type multi X-ray source 30 described above will acquire X-ray projection data between the respective multi X-ray sources (e.g., between m(1, 1) and m(1, 2) of the multi X-ray source). It is therefore possible to implement a proximity projection imaging apparatus which can acquire high-resolution images.

Figure 6:
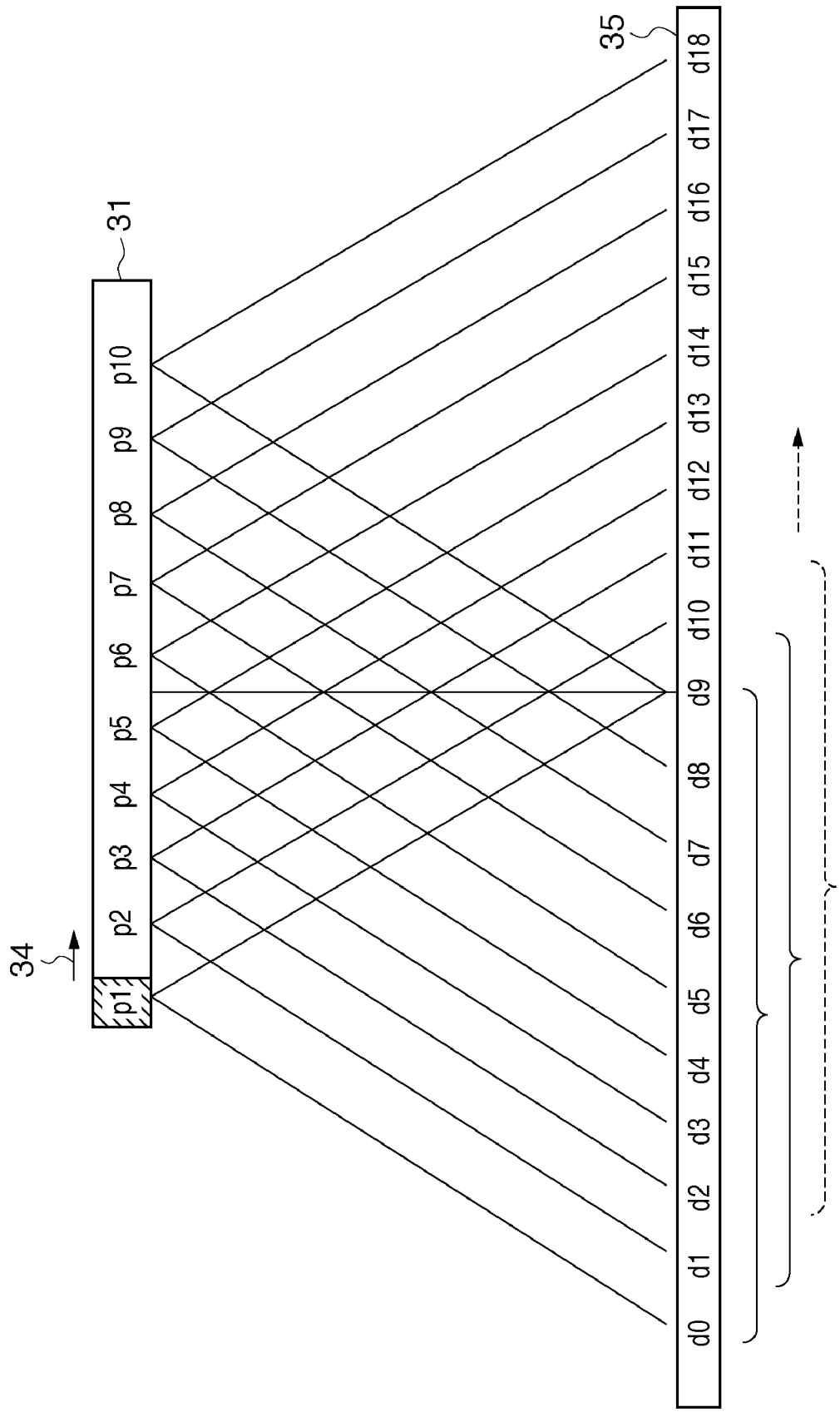
FIG. 6 is a view for explaining the movement of the irradiation area of a multi X-ray source and the detection of X-rays.

The manner of how X-ray imaging is actually performed while X-ray sources are moved by using the scanning type multi X-ray source 30 will be described with reference to FIG. 6. Consider first one X-ray source m(k, 1) of the X-ray source array in a multi X-ray unit. First of all, when the multi X-ray source m(k, 1) emits X-rays at a position p1, detectors d0 to d9 detect the transmitted X-rays. The scanning mechanism 34 then moves the position of the multi X-ray source to p2. When the multi X-ray source m(k, 1) emits X-rays at a position p2 after the movement, detectors d1 to d10 detect the transmitted X-rays. In this manner, transmission X-ray data are acquired while the multi X-ray source is repeatedly moved to the adjacent multi X-ray source from p1 to p10, and the X-ray sources of the radiation source array in each unit repeatedly emit X-rays.

Figure 7:
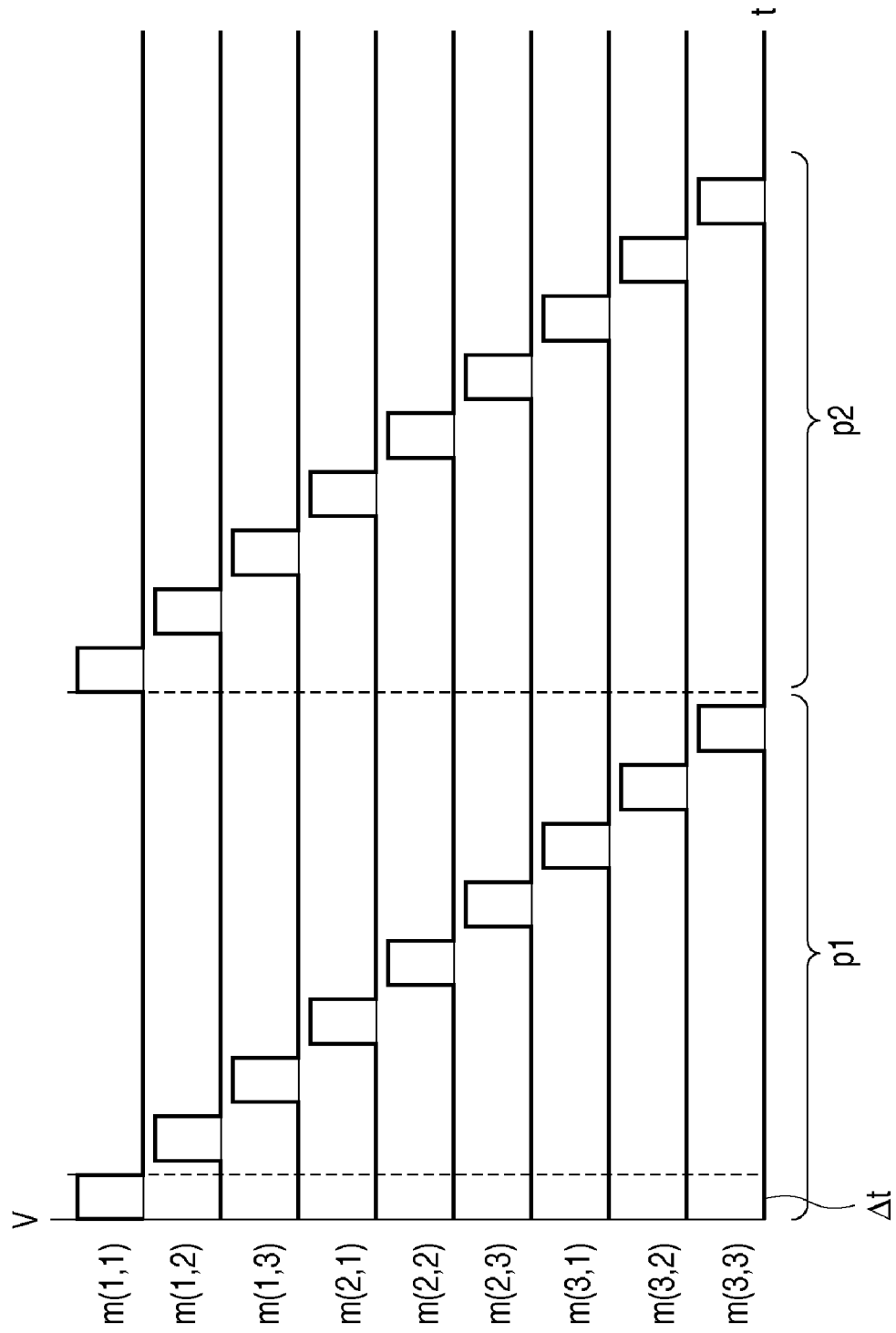
FIG. 7 is a view for explaining the driving of an X-ray source array in a basic unit.

FIG. 7 shows the temporal operation of each X-ray source of the radiation source array in each unit in association with the above X-ray irradiation method. The X-ray source m(1, 1) is turned on at the position p1 for a time Δt. Subsequently, the X-ray sources are sequentially switched and turned on up to the X-ray source m(3, 3). The position of the multi X-ray source 31 then moves from p1 to p2, and X-rays are repeatedly turned on in the same manner.

The flowchart of FIG. 12 summarizes, as follows, the imaging operation of the X-ray imaging apparatus according to the first embodiment described above. Assume that X-ray sources are arrayed in a 3×3 matrix in the multi X-ray unit 32, as shown in FIG. 4, and both kmax and lmax in the flowchart are 3.

The controller 300 moves the multi X-ray source 31 to a reference position having a predetermined positional relationship with the detector 35 by using the scanning mechanism 34 (step S101). First of all, the controller 300 selects the X-ray source m(1, 1) of each multi X-ray unit, and executes the acquisition processing of making these X-ray sources simultaneously generate X-rays and making the detector 35 obtain X-ray image information (steps S102 and S103). Thereafter, the controller 300 sequentially selects and drives the X-ray sources m(1, 2) and m(1, 3) and repeats the above acquisition processing. That is, the controller 300 sequentially drives the X-ray sources m(1, 2) and m(1, 3) of each multi X-ray unit, and obtains the respective pieces of X-ray image information by using the detector 35 (steps S103 to S105).

Subsequently, the controller 300 repeats steps S103 to S105 described above with respect to k=2. That is, the controller 300 sequentially drives the X-ray sources m(2, 1) to m(2, 3) of each multi X-ray unit, and obtains X-ray image information by using the detector 35 (steps S106 and S107). Likewise, the controller 300 repeats steps S103 to S105 described above with respect to k=3. That is, the controller 300 sequentially drives the X-ray sources m(3, 1) to m(3, 3) of each multi X-ray unit, and obtains X-ray image information by using the detector 35 (steps S106 and S107). Upon completing the acquisition processing using all the X-ray sources in each multi X-ray unit, the controller 300 moves the multi X-ray source 31 from, for example, p1 to p2 in FIG. 6 by using the scanning mechanism 34. The controller 300 then repeats the processing in steps S102 to 5107 described above at the position p2 (steps S108 and S109).

When the multi X-ray source 31 reaches the position p10 and X-ray irradiation and detection at the position p10 are completed by repeating the above processing, the process advances from step S108 to step S110. In step S110, the controller 300 obtains an X-ray projection image by performing image generation using the X-ray image information acquired in step S103.

As described above, the first embodiment can acquire the data of a high-quality X-ray projection image using the multi X-ray source by causing the multi X-ray source to perform X-ray irradiation (scanning) while moving the multi X-ray source within the plane of the multi X-ray source and in the range of the X-ray source intervals. That is, since high-resolution X-ray imaging can be performed in spite of the fact that the multi X-ray source is placed near the two-dimensional flat type detector, a high-resolution and compact X-ray projection imaging apparatus can be obtained. In addition, since imaging is performed while X-ray sources are placed near the detector, the power of X-rays can be efficiently used. This can obtain a low-cost X-ray apparatus with reduced leakage X-rays to the surroundings. In addition, since the X-ray sources of the multi X-ray source which are to be simultaneously driven are selected so as to avoid interference of X-rays from the respective X-ray sources on the detection surface, interference of X-rays from different X-ray sources can be prevented, and an X-ray image with higher resolution can be obtained.

Second Embodiment

The intensity of X-rays obtained by the X-ray sources of the radiation source array in each multi X-ray unit depends on the melting point of an X-ray target material or its cooling system, an accelerating voltage for electron beams, a current value, a focus size, an irradiation time, an X-ray extraction method, and the like.

Since the maximum X-ray power of a conventional X-ray tube is determined by the temperature limit of an X-ray target material to be used, thermal diffusion is performed by mechanically rotating the X-ray target so as to sequentially move the irradiation position, thereby extracting a higher X-ray power. In contrast to this, the scheme used by this embodiment performs thermal diffusion of an X-ray target by electrically scanning the position of the multi electron source to allow the injection of higher X-ray power. These specific examples will be described with reference to FIG. 8.

Figure 8:
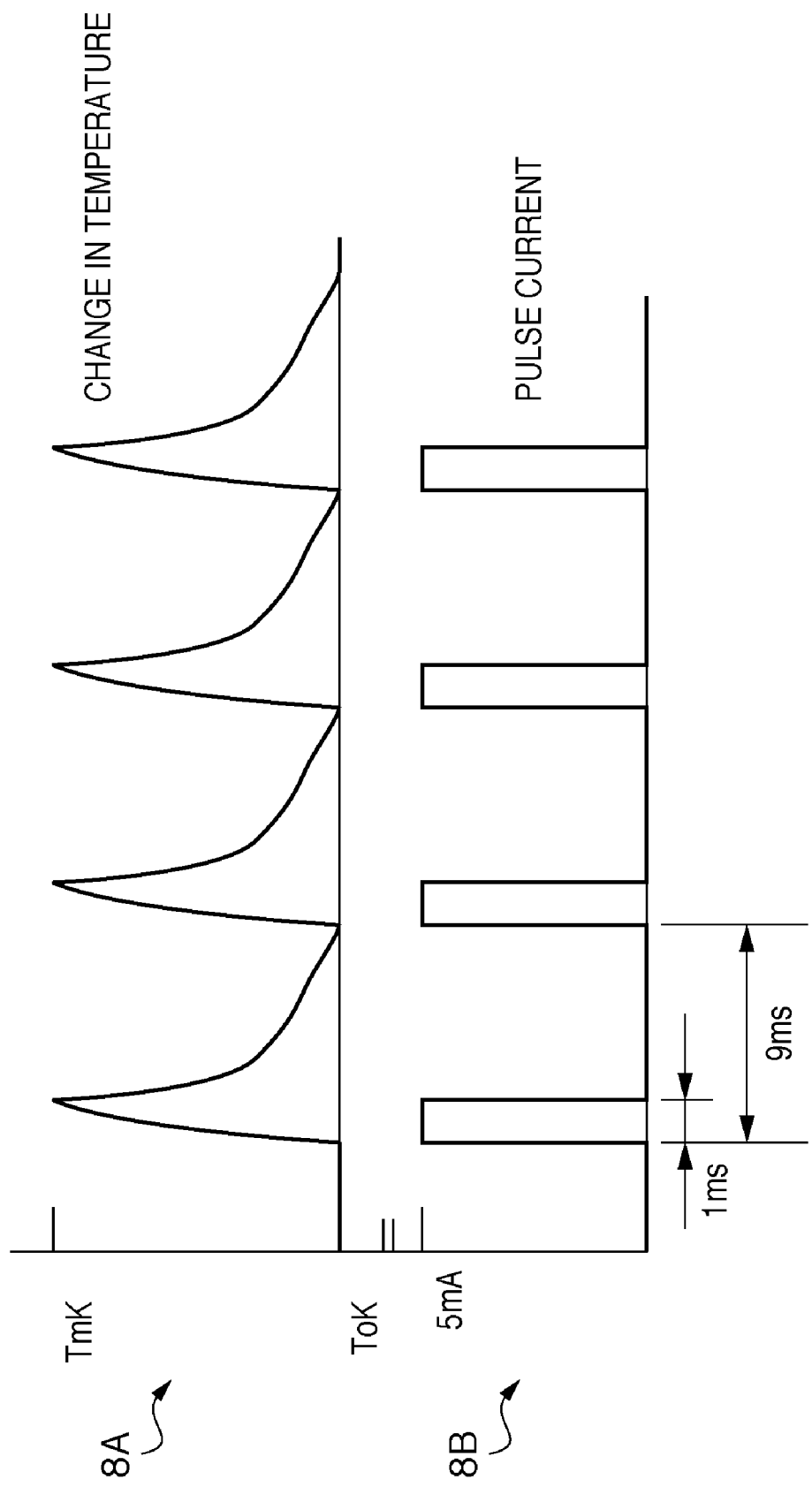
FIG. 8 explains the association between changes in the surface temperature of an X-ray target and the application of pulse currents for X-ray irradiation.

FIG. 8 shows temporal changes in the temperature of the surface of an X-ray target when the target is irradiated with an electron beam. "A" and "B" in FIG. 8 respectively represent examples of the waveform of an electron current ("8B" in FIG. 8) at the time of the generation of a rectangular pulse signal as a driving signal for an electron source, and changes in the surface temperature of the X-ray target ("8A" in FIG. 8). A temperature Tm of an X-ray target quickly rises for 1 ms during which X-rays are generated by pulse currents, and the surface temperature of the X-ray target is restored to an initial temperature state "To" owing to heat conduction to the peripheral structure for about 9 ms from the time when a pulse current is turned off. In this embodiment, in order to effectively generate X-rays from the multi X-ray source, one X-ray source of each multi X-ray unit 32 in FIG. 3 is always turned on. The time during which all the X-ray sources of the radiation source array in each basic unit are OFF is set to a cooling time for the surface temperature of the X-ray target. This makes it possible to form a high-power X-ray source exploiting the characteristics of the multi X-ray source.

In order to safely operating such a multi X-ray source while extracting power from it, it is important to manage the setting about an X-ray irradiation time Δt of each radiation source array in each basic unit shown in FIG. 7 so as not to exceed the temperature limit of the X-ray target.

For example, the surface temperature Tm of the X-ray target is determined by parameters including the current, voltage, and Δt of the multi X-ray source in association with a temperature allowable value Tmax of the X-ray target. Therefore, Δt is set to hold $Tm = T(\text{voltage}, \text{current}, \Delta t)$ $Tm < Tmax$ The safety of the multi X-ray source can be improved by having these data in advance as a function or data, and by determining a maximum mAs value to be applied to the X-ray target. In addition, the time interval of generation of X-rays from one X-ray source, that is, the time interval of irradiation of electron beams, is at least the period during which the temperature of the X-ray target which has been raised by the irradiation of an electron beam lowers to the first temperature or lower (To or lower).

Note that if the X-ray dose required for an X-ray projection image exceeds this mAs value, it is possible to make setting so as to cause the multi X-ray source to automatically repeat necessary X-ray irradiation at the same position. Using this method can perform imaging while the performance of the multi X-ray source is maximized.

Third Embodiment

The first embodiment has exemplified the projection imaging method in a case in which the multi X-ray source having the two-dimensional array is used. The third embodiment will exemplify an imaging apparatus and an imaging method with reference to FIG. 9 in a case in which a multi X-ray source having a one-dimensional array is used.

Figure 9:
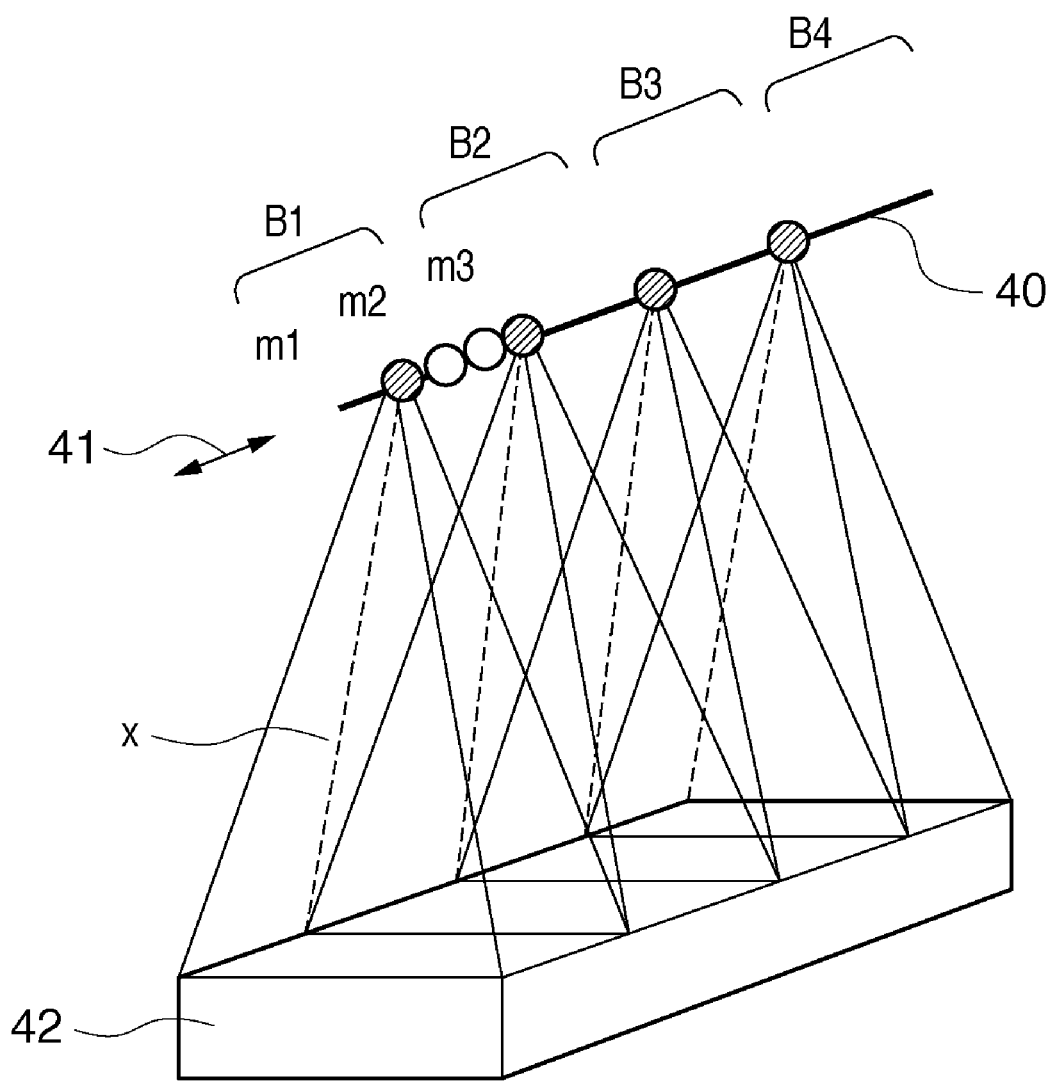
FIG. 9 is a view showing an application example of a one-dimensional array multi X-ray source according to the third embodiment.

An elongated detector 42 is placed at a position facing a multi X-ray source 40 having a one-dimensional array. An object is placed in a direction parallel to the multi X-ray source 40 with the one-dimensional array and the detector 42. The multi X-ray source 40 includes a one-dimensional array multi X-ray unit and X-ray sources constituting a radiation source array in a one-dimensional unit. In the case of FIG. 9, each multi X-ray unit includes X-ray sources m(1, 1), m(1, 2), and m(1, 3).

When the multi X-ray source is made to generate X-rays by repeating the operation of sequentially turning on X-ray sources m(1, 1), m(1, 2), and m(1, 3) and moving the multi X-ray source 40 in the array direction, thereby acquiring X-ray projection data. At the stage at which the multi X-ray source 40 is scanned by a width corresponding to the array interval of X-ray sources, an object is moved in a direction perpendicular to the array direction 41 of the X-ray sources in the multi X-ray source 40. Note that in place of moving the object, it is possible to use a method of simultaneously moving the multi X-ray source 40 and the detector 42 in a direction perpendicular to the array direction of the X-ray sources.

Figure 10:
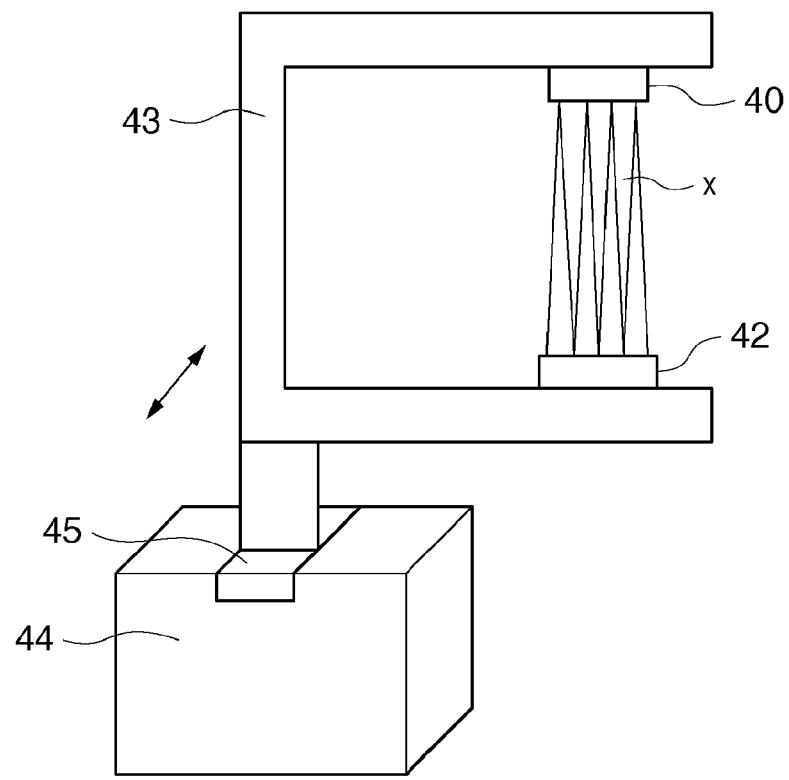
FIG. 10 is a view showing an example of an X-ray projection apparatus using the one-dimensional array multi X-ray source according to the third embodiment.

FIG. 10 is a view showing an example of an arrangement configured to move the multi X-ray source 40 and the detector 42 together. In this case, the multi X-ray source 40 and the detector 42 are fixed by a support unit 43. A driving unit 45 on a base 44 moves the multi X-ray source 40 and the detector 42 in synchronism with the generation of X-rays from X-ray sources.

As described above, the third embodiment uses the multi X-ray source 40 having a one-dimensional array of a plurality of X-ray focuses. A controller 300 causes the multi X-ray source 40 to emit X-rays while causing a scanning mechanism 34 to move a multi X-ray source 40 in an array direction 41 of the plurality of X-ray focuses, thereby acquiring X-ray detection signals using the detector 42. The controller 300 then obtains two-dimensional X-ray image information by repeating this processing while moving the multi X-ray source 40 in a direction perpendicular to the array direction 41. Note that if the detector 42 has a sufficiently large detection area, it is possible to move only the multi X-ray source 40 in the direction perpendicular to the array direction 41 of the multi X-ray source 40. The arrangement shown in FIGS. 9 and 10 is configured to move both the multi X-ray source 40 and the detector 42 in the direction perpendicular to the array direction 41 because the detection surface of the detector 42 corresponds to an area of the multi X-ray source 40 which corresponds to one irradiation.

As described above, according to the third embodiment, it is possible to form an X-ray projection apparatus using a very compact, low-cost scanning type multi X-ray source by using a one-dimensional multi X-ray source.

Fourth Embodiment

Figure 11:
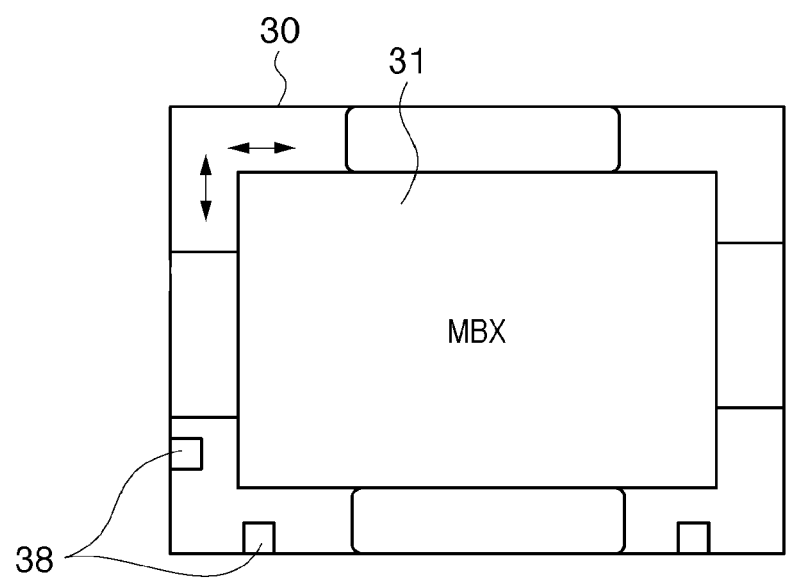
FIG. 11 is a view for explaining a scanning type multi X-ray source according to the fourth embodiment.

FIG. 11 shows a method of obtaining high-quality X-ray projection data in the driving mechanism of a scanning type multi X-ray source. In order to obtain a high-resolution X-ray image, it is necessary to set the accuracy of attitude control of the multi X-ray source to several 10 μm or less. A simple method of implementing this is to attach a position detector 38 using an optical means to a scanning type multi X-ray source 30 according to the fourth embodiment, in addition to a scanning mechanism 34 for a multi X-ray source 31, to read the position of the multi X-ray source 31. The position detector 38 reads the position of the multi X-ray source 31 at the time of X-ray irradiation. It is possible to convert X-ray transmission intensity data (detection signal) into a high-resolution projection image by using this position data as X-ray source position correction data at the time of conversion from the X-ray transmission intensity data into the X-ray projection image.

As has been described above, according to each embodiment described above, it is possible to convert the transmission X-ray data acquired by the scanning type multi X-ray apparatus into an X-ray projection image by using a conventional method of obtaining a tomogram. This makes it possible to provide a compact X-ray projection imaging apparatus which exploits the characteristics of a multi X-ray source and can acquire a high-resolution image.

Other Embodiments

In addition, the present invention is implemented by executing the following processing. That is, this processing is to supply software (program) for implementing the functions of the above embodiments to a system or apparatus via a network or various kinds of storage media and cause the computer (or CPU, MPU, or the like) of the system or apparatus to read out and execute the program.

The present invention is not limited to the above embodiments and various changes and modifications can be made within the spirit and scope of the present invention. Therefore, to apprise the public of the scope of the present invention, the following claims are made.

This application claims the benefit of Japanese Patent Application No. 2008-239754, filed Sep. 18, 2008, which is hereby incorporated by reference herein in its entirety.

The invention claimed is:

1. An X-ray imaging apparatus comprising:
a multi X-ray source which includes a plurality of X-ray focuses to generate X-rays by irradiating X-ray targets with electron beams;
a detector which detects X-rays which have been emitted from said multi X-ray source and have reached a detection surface;
a moving unit configured to move said multi X-ray source within a plane facing the detection surface;
an acquisition unit configured to acquire an X-ray detection signal from said detector for each irradiation by performing X-ray irradiation a plurality of number of times using said multi X-ray source while shifting said multi X-ray source relative to the detection surface by using said moving unit; and
a generating unit configured to generate an X-ray projection image based on a plurality of X-ray detection signals acquired by said acquisition unit.

2. The X-ray imaging apparatus according to claim 1, wherein said acquisition unit acquires a plurality of X-ray detection signals from said detector by performing X-ray irradiation a plurality of number of times using said multi X-ray source while moving said multi X-ray source over a distance to an adjacent X-ray focus using said moving unit.

3. The X-ray imaging apparatus according to claim 1, wherein said acquisition unit acquires X-ray detection signals by said detector by dividing the plurality of X-ray focuses into a plurality of groups so as to prevent X-rays from interfering with each other on the detection surface even if the X-rays are simultaneously generated, and generating X-rays from the plurality of X-ray focuses for each group, and
moves said multi X-ray source by using said moving unit after acquisition of detection signals is complete with respect to all the plurality of groups.

4. The X-ray imaging apparatus according to claim 1, wherein an interval at which the electron beam is irradiated to generate X-rays from each of the plurality of X-ray focuses is a period required to lower a temperature of the X-ray target, which has been increased by at least irradiation of the electron beam, to not more than a first temperature, and a time during which the electron beam is irradiated is a time during which an increase in temperature of the X-ray target due to irradiation of the electron beam does not exceed an allowable temperature value.

5. The X-ray imaging apparatus according to claim 1, wherein
the plurality of X-ray focuses are two-dimensionally arrayed, and
said moving unit moves said multi X-ray source in a two-dimensional direction.

6. The X-ray imaging apparatus according to claim 1, wherein
the plurality of X-ray focuses are one-dimensionally arrayed, and
said acquisition unit executes acquisition processing of acquiring X-ray detection signals using said detector by causing said multi X-ray source to irradiate X-rays while moving said multi X-ray source in an array direction of the plurality of X-ray focuses using said moving unit, and repeats the acquisition processing while moving said multi X-ray source in a direction perpendicular to the array direction using said moving unit.

7. The X-ray imaging apparatus according to claim 6, wherein said moving unit moves said multi X-ray source and said detector together in the direction perpendicular to the array direction.

8. The X-ray imaging apparatus according to claim 1, further comprising a position detection unit configured to detect a position of said multi X-ray source, wherein said generating unit generates an X-ray projection image by correcting the detection signal based on the position of said multi X-ray source which is detected by said position detection unit.

9. A control method for an X-ray imaging apparatus including: a multi X-ray source which includes a plurality of X-ray focuses to generate X-rays by irradiating X-ray targets with electron beams; a detector which detects X-rays which have been emitted from the multi X-ray source and have reached a detection surface; and a moving unit configured to move the multi X-ray source within a plane facing the detection surface, said method comprising:

an acquisition step of acquiring X-ray detection signals from the detector for each irradiation by causing the multi X-ray source to perform X-ray irradiation a plurality of number of times while shifting the multi X-ray source relative to the detection surface by using the moving unit; and a generating step of generating an X-ray projection image based on a plurality of X-ray detection signals acquired in the acquisition step.

10. A non-transitory computer-readable storage medium storing a program for causing a computer to execute a control method for an X-ray imaging apparatus defined in claim 9.

11. An X-ray imaging apparatus comprising:
a multi X-ray source which includes a plurality of X-ray focuses to generate X-rays by irradiating X-ray targets with electron beams;
a detector which detects X-rays which have been emitted from said multi X-ray source and have reached a detection surface;
a moving unit configured to move said multi X-ray source;
an acquisition unit configured to acquire an X-ray detection signal from said detector for each irradiation by performing X-ray irradiation a plurality of number of times using said multi X-ray source while shifting said multi X-ray source relative to the detection surface by using said moving unit; and
a generating unit configured to generate an X-ray projection image based on a plurality of X-ray detection signals acquired by said acquisition unit.

12. The X-ray imaging apparatus according to claim 11, wherein said acquisition unit acquires a plurality of X-ray detection signals from said detector by performing X-ray irradiation a plurality of number of times using said multi X-ray source while moving said multi X-ray source over a distance to an adjacent X-ray focus using said moving unit.

13. The X-ray imaging apparatus according to claim 11, wherein said acquisition unit acquires X-ray detection signals by said detector by dividing the plurality of X-ray focuses into a plurality of groups so as to prevent X-rays from interfering with each other on the detection surface even if the X-rays are simultaneously generated, and generating X-rays from the plurality of X-ray focuses for each group, and moves said multi X-ray source by using said moving unit after acquisition of detection signals is complete with respect to all the plurality of groups.

14. The X-ray imaging apparatus according to claim 11, wherein an interval at which the electron beam is irradiated to generate X-rays from each of the plurality of X-ray focuses is a period required to lower a temperature of the X-ray target, which has been increased by at least irradiation of the electron beam, to not more than a first temperature, and a time during which the electron beam is irradiated is a time during which an increase in temperature of the X-ray target due to irradiation of the electron beam does not exceed an allowable temperature value.

15. The X-ray imaging apparatus according to claim 11, wherein
the plurality of X-ray focuses are two-dimensionally arrayed, and
said moving unit moves said multi X-ray source in a two-dimensional direction.

16. The X-ray imaging apparatus according to claim 11, wherein
the plurality of X-ray focuses are one-dimensionally arrayed, and
said acquisition unit executes acquisition processing of acquiring X-ray detection signals using said detector by causing said multi X-ray source to irradiate X-rays while moving said multi X-ray source in an array direction of the plurality of X-ray focuses using said moving unit, and
repeats the acquisition processing while moving said multi X-ray source in a direction perpendicular to the array direction using said moving unit.

17. The X-ray imaging apparatus according to claim 16, wherein said moving unit moves said multi X-ray source and said detector together in the direction perpendicular to the array direction.

18. The X-ray imaging apparatus according to claim 11, further comprising a position detection unit configured to detect a position of said multi X-ray source, wherein said generating unit generates an X-ray projection image by correcting the detection signal based on the position of said multi X-ray source which is detected by said position detection unit.

19. A control method for an X-ray imaging apparatus including: a multi X-ray source which includes a plurality of X-ray focuses to generate X-rays by irradiating X-ray targets with electron beams; a detector which detects X-rays which have been emitted from the multi X-ray source and have reached a detection surface; and a moving unit configured to move the multi X-ray source, said method comprising:

an acquisition step of acquiring X-ray detection signals from the detector for each irradiation by causing the multi X-ray source to perform X-ray irradiation a plurality of number of times while shifting the multi X-ray source relative to the detection surface by using the moving unit; and a generating step of generating an X-ray projection image based on a plurality of X-ray detection signals acquired in the acquisition step.

20. A non-transitory computer-readable storage medium storing a program for causing a computer to execute a control method for an X-ray imaging apparatus defined in claim 19.

* * * * *